United States Patent [19]

Glockner et al.

[11] 4,078,011
[45] Mar. 7, 1978

[54] SELECTIVE HYDROGENATION OF DIENES USING NICKEL/ALUMINUM SULFIDE CATALYST

[75] Inventors: Peter W. Glockner, Houston; J. David Richardson, Sugarland, both of Tex.

[73] Assignee: Shell Oil Company, Houston, Tex.

[21] Appl. No.: 789,893

[22] Filed: Apr. 22, 1977

[51] Int. Cl.² .................. C07C 11/00; C07C 5/06; B01J 27/04
[52] U.S. Cl. .................. 260/677 H; 252/439; 208/255; 260/683.9; 423/561
[58] Field of Search .................. 260/677 H, 683.9; 208/255; 252/439

[56] References Cited

U.S. PATENT DOCUMENTS

| | | | |
|---|---|---|---|
| 2,402,493 | 6/1946 | Greensfelder et al. | 260/677 H |
| 3,223,652 | 12/1965 | Erickson et al. | 252/439 |

*Primary Examiner*—Winston A. Douglas
*Assistant Examiner*—P. E. Konopka
*Attorney, Agent, or Firm*—Dean F. Vance

[57] ABSTRACT

A process for the selective hydrogenation of dienes present in a $C_{3-6}$ mixed hydrocarbon stream is disclosed wherein the hydrocarbon stream is contacted with added hydrogen in the presence of a catalyst comprising about 1 to 30% by weight nickel on an aluminum sulfide support.

8 Claims, No Drawings

SELECTIVE HYDROGENATION OF DIENES USING NICKEL/ALUMINUM SULFIDE CATALYST

BACKGROUND OF THE INVENTION

The olefin stream employed in the standard refinery alkylation processes is principally that obtained from the thermal or catalytic cracking of higher boiling hydrocarbons or from a hydrocarbon coking operation. This olefin stream often contains a significant amount, e.g. about 1% or more, of dienes. Even this small amount of diene in the feed to the alkylation process has been widely recognized as being undesirable for the one reason, among others, that it results in a greatly increased consumption of acid made necessary by the formation of tarry acid-diene condensation products. Other olefin streams may contain greater amounts of dienes, such as 50% or greater dienes.

A process employing a novel catalyst has now been found that results in the selective hydrogenation of the diene components without the undesirable hydrogenation of the olefins.

SUMMARY OF THE INVENTION

A novel process for the selective hydrogenation of dienes in a mixed hydrocarbon stream composed essentially of hydrocarbons, especially including olefins, in the range of 3-6 carbon atoms, is disclosed, which process comprises contacting said mixed hydrocarbon stream with added hydrogen at a temperature of between about 150° F and about 500° F and a pressure of 1 to 1000 atmospheres in the presence of a catalyst comprising about 1 to about 30 percent by weight nickel on an aluminum sulfide support. The key to the present invention is the use of the aluminum sulfide support in place of the usual aluminum oxide support. The Ni/$Al_2S_3$ catalyst has a number of advantages over the Ni/$Al_2O_3$ catalyst. For one, the Ni/$Al_2S_3$ catalyst is not as susceptible to sulfur poisoning as the Ni/$Al_2O_3$ catalyst. For another, the Ni/$Al_2O_3$ catalyst possesses a much greater activity and selectivity than the Ni/$Al_2O_3$ catalyst. As shown in the following illustrative embodiment, the present Ni/$Al_2S_3$ catalyst gave a conversion of 97.5% and a selectivity of 97.1% at 248° F, whereas a commercial sulfided Ni/$Al_2O_3$ catalyst required a much higher temperature of around 375° F to give comparable conversion and selectivity results. Further, while it is known that supported nickel catalysts are difficult to reduce, the Ni/$Al_2S_3$ catalyst was relatively easy to reduce. For example, it is possible to reduce a Ni/$Al_2S_3$ catalyst over a temperature range of 250°-450° C, whereas the corresponding range for Ni/$Al_2O_3$ is 360°-700° C.

It is also significant to note that sulfiding a Ni/$Al_2O_3$ catalyst does not result in the conversion of any of the $Al_2O_3$ to $Al_2S_3$. Rather, the most likely result is the conversion of some of the nickel to nickel sulfide.

DETAILED DESCRIPTION OF THE INVENTION

The mixed hydrocarbon stream herein employed may be obtained from any source, and typically contains hydrocarbons in the $C_3$ to $C_6$ range. Preferably, the stream contains a large amount of olefins, such as from 10 to 60%, and a smaller amount of dienes, such as from 0.1 to 20%. The relative amounts of the diene and olefin are not critical, as the present catalyst is useful over a wide range of concentrations. In some cases, the mixed hydrocarbon stream may even contain 50-70% dienes.

The selective hydrogenation takes place in the liquid phase at a temperature of between about 150° F and about 500° F and a pressure of about 1 atmosphere and about 1000 atmospheres. Preferred conditions are a temperature of between about 200° F and about 400° F and a pressure of between about 10 atmospheres and about 200 atmospheres.

The hydrogen added in the process is maintained as low as possible (for economic reasons) but at least in excess of the stoichiometric requirement for full conversion of the dienes to monoolefins. In practice, the hydrogen is employed in a ratio of at least about 1.5 moles hydrogen per mole diene in the hydrocarbon feed, and generally less than about 20 moles hydrogen per mole diene.

The liquid hourly space velocity, defined as the volume of liquid hydrocarbon feed per volume of catalyst in the reactor, is typically between about 1 and about 15, preferably between about 2 and about 10.

As stated above, the key to the present invention lies in the use of a catalytic amount of nickel metal on an aluminum sulfide support instead of an aluminum oxide support.

The $Al_2S_3$ support may be prepared by any convenient method. However, a much preferred $Al_2S_3$ is prepared by the sulfiding of a trialkyl aluminum compound having 1 to 5 carbon atoms. The $Al_2S_3$ is typically prepared by first dissolving the trialkyl aluminum in an aprotic solvent. Then the solution is added to a reactor along with a stoichiometric amount of hydrogen sulfide. The reactor is then heated to a temperature of between about 100° F and about 400° F and a pressure of between about 100 psig and 1000 psig until the reaction is complete, typically between about 1 hour and about 10 hours. Anhydrous conditions are maintained throughout. Suitable aprotic solvents include toluene, dioxone, tetrahydrofuran, various ethers, and paraffinic hydrocarbons. The preferred solvent is toluene. The recovered aluminum sulfide possesses a very high surface area, even after calcination at high temperatures. See Table I in the Illustrative Embodiments. Typically, the recovered aluminum sulfide is also calcined under anhydrous condition of a temperature of between about 200° C and about 600° C.

The nickel is placed on the support by any suitable method. However, wet impregnation cannot be employed. Typically, the nickel is placed on the $Al_2S_3$ support by contacting the $Al_2S_3$ with a solution of a nickel compound or complex in an aprotic solvent, and then heating the resulting solution under refluxing conditions for between about 1 hour and about 10 hours. The solution is then typically cooled, filtered and dried by vacuum.

Suitable nickel compounds or complexes are those that dissolve in aprotic solvents such as nickel acetylacetonate, nickel octoate, bis-salicylaldoxime nickel, bis-salicylaldehyde nickel, bis-cyclooctadiene nickel and nickel chloride-tetrahydrofuran complex, bis($\pi$-allyl)-nickel chloride, and bis(tetrahydrofuran)nickel dibromide. A preferred nickel complex is nickel acetylacetonate.

The amount of nickel compound or complex employed should be sufficient to result in a catalyst containing about 1 to about 30 percent by weight nickel, preferably about 10 to about 25 percent by weight nickel.

The recovered nickel catalyst is then reduced at a temperature of between about 500° F and about 1000° F, preferably between about 800° F and about 900° F. The reduced catalyst possesses excellent activity and selectivity for the selective hydrogenation of dienes to monoolefins.

The invention is further illustrated by means of the following illustrative embodiments, which are given for the purpose of illustration only and are not meant to limit the invention to the particular reactants and amounts disclosed.

In all illustrative embodiments, the aluminum sulfide employed was prepared by the following process. A 100 milliliter stainless steel autoclave was cleaned and dried over night in an oven at 120° C. After assembly, the autoclave was evacuated and purged with dry nitrogen three times. With the autoclave under a dry nitrogen atmosphere, a 30 milliliter portion of 25% by weight triethylaluminum in toluene was added. The autoclave was cooled in a dry-ice/isopropyl alcohol bath, and 7 grams of hydrogen sulfide was added. The autoclave was sealed and heated, with stirring, at 105° C for 1.5 hours. The pressure was maintained at 550–600 psig. The apparatus was then cooled, purged with dry nitrogen for 1 hour and evacuated for 1 hour to remove the toluene solvent. The white product (aluminum sulfide) was removed in the dry box and stored under nitrogen.

The surface area and pore volume of the aluminum sulfide produced above was determined as a function of calcination temperature. The results are shown below in Table I.

TABLE I
SURFACE AREA AND PORE VOLUME OF ALUMINUM SULFIDE AS A FUNCTION OF CALCINATION TEMPERATURE

| Sample Number | Calcination Temperature,° C | Surface Area m$^2$/g | Pore Volume cm$^3$/g |
|---|---|---|---|
| A | 200 | 688 | 0.89 |
| B | 400 | 518 | 0.67 |
| C | 500 | 223 | 0.46 |
| D | 550 | 70 | 0.27 |

As expected, both surface area and pore volume decrease as the temperature is increased. However, the magnitude of the surface area, even after calcination at 550° C, was quite high. It appears that the aluminum sulfide prepared as above initially precipitates out as an amorphous solid with a very high surface area. Upon heating at higher temperatures the material begins to crystallize, accompanied by a loss of surface area and pore volume.

ILLUSTRATIVE EMBODIMENT I

In Illustrative Embodiment I, a nickel on aluminum sulfide (Ni/Al$_2$S$_3$) catalyst was employed in the selective hydrogenation of isoprene. The Ni/Al$_2$S$_3$ catalyst was prepared by adding 20 grams of the aluminum sulfide and 100 milliliters of dry toluene to a 250 milliliter round-bottomed flask under nitrogen pressure. To this mixture was added 13.4 grams of nickel acetylacetonate. The mixture was heated at reflux temperature for 3 hours, cooled, filtered under nitrogen and dried by vacuum. The residue was sealed in a 6 inch piece of gum rubber tubing, pressed hydrostatically at 20,000 psig, ground and sieved (in the dry box) to 16–45 mesh.

All test reactions were run in a standard microreactor set-up. The catalysts were loaded into 18 inch stainless steel reactor tubes while in the dry box. The volume of catalyst used was 10.4 cc. The catalyst prior to reaction was reduced at 400° F for 2 hours, 600° F for 1 hour and 700° F for 2 hours (except where noted otherwise). All feedstocks were dried over molecular sieves prior to use. The feedstock employed was 60% by volume isoprene and 40% by volume normal hexane. The results are presented below in Table II.

TABLE II
SELECTIVE HYDROGENATION OF ISOPRENE OVER A Ni/Al$_2$S$_3$ CATALYST

| Hours On Stream | ° F Temp. | (1) | (2) | (3) | (4) | (5) | % Conv. | Select. |
|---|---|---|---|---|---|---|---|---|
| 2.0 | 250 | 1.92 | 0.34 | 5.19 | 32.89 | 18.06 | 44.0 | 98.7 |
| 3.5 | 300 | 3.11 | 0.36 | 8.53 | 12.47 | 33.93 | 79.0 | 99.2 |
| 5.0 | " | 2.66 | 0.36 | 7.49 | 16.66 | 29.68 | 70.7 | 99.1 |
| 6.5 | 350 | 2.04 | 0.52 | 7.24 | 14.96 | 31.85 | 73.6 | 98.7 |
| 7.5 | " | 1.60 | 0.47 | 5.62 | 23.23 | 26.06 | 59.2 | 98.6 |
| REDUCED AT 800° F | | | | | | | | |
| 8.5 | 350 | 0.40 | 12.45 | 6.76 | 0.63 | 32.76 | 98.8 | 76.2 |
| 9.0 | " | 0.44 | 11.36 | 7.31 | 0.47 | 34.75 | 99.1 | 78.91 |
| 10.0 | 300 | 0.47 | 5.37 | 7.69 | 0.29 | 41.14 | 99.5 | 90.2 |
| 11.0 | 240 | 1.32 | 2.76 | 7.63 | 1.04 | 42.22 | 98.1 | 94.9 |
| 11.5 | 248 | 2.31 | 1.58 | 7.89 | 1.41 | 43.3 | 97.5 | 97.1 |

Pressure = 1000 psig
H$_2$/oil = 5.4
LHSV = 6.7
% Nickel = 24%w
(1) 3-methyl-1-butene
(2) 2-methylbutane
(3) 2-methyl-1-butene
(4) 2-methyl,1,3-butadiene(isoprene)
(5) 2-methyl-2-butene The initial results showed good selectivity but poor conversion. The feed was removed and the catalyst was further reduced at 800° F for one hour. This caused a dramatic increase in conversion, accompanied by a decrease in selectivity. The temperature was adjusted until, at 248° F, a conversion of 97.5% and selectivity of 97.1% were obtained. A commercial Ni/Al$_2$O$_3$ (Harshaw Ni/Al$_2$O$_3$, Ni-0301T ⅛ inch, Lot 47) was sulfided with a 5% H$_2$S/H$_2$ mixture and tested on the same feed. The data in Table III show that this catalyst gives comparable conversion and selectivity only at 375° F. At 250° F the conversion with the Harshaw catalyst is less than that with the Ni/Al$_2$S$_3$ catalyst by a factor of 21. Neither of the catalysts were tested over a long enough period of time to allow a comparison of their respective stabilities. The metal loading for the sulfide-based catalyst was 25% Ni while for the Harshaw catalyst it was only 9.8% Ni. However, the activity difference is much greater than can be explained just by the difference in metal loading.

TABLE III

SELECTIVE HYDROGENATION OF ISOPRENE OVER A Ni/Al$_2$O$_3$ CATALYST

| Hours On Stream | °F Temp. | ⟋⟍ | ⟋⟍ | ∥⟍ | ∥⟍ | ⟝⟍ | % Conv. | Select. |
|---|---|---|---|---|---|---|---|---|
| 1.0 | 250 | .15 | — | .54 | 48.67 | 1.65 | 4.6 | 100 |
| 2.0 | 300 | .13 | .07 | 1.83 | 36.26 | 6.83 | 19.7 | 99.2 |
| 5.0 | 350 | 4.08 | .19 | 5.86 | 10.52 | 24.18 | 76.5 | 99.1 |
| 6.0 | " | 4.13 | .21 | 6.52 | 3.01 | 27.80 | 92.8 | 99.5 |
| 6.5 | " | 4.40 | .22 | 7.46 | 1.88 | 30.75 | 95.8 | 99.5 |
| 7.0 | 375 | 2.64 | .67 | 8.49 | 0.79 | 37.06 | 98.4 | 98.6 |

Pressure = 1000 psig
H$_2$/oil = 5.4
LHSV = 2.82
% Nickel = 9.81%

Supported nickel catalysts are known to be difficult to reduce. The apparent explanation is that the nickel and alumina support interact to form a nickel spinel which requires a much higher reduction temperature than does nickel oxide alone. A metal-support interaction of this nature may not occur between nickel and aluminum sulfide. If not, the Ni/Al$_2$S$_3$ catalyst may be more easily reduced and consequently, more active. To compare the relative reducibility of the two catalysts a temperature programmed reduction profile was obtained for each. The Ni/Al$_2$S$_3$ catalyst was reduced over the temperature range 250°–450° C, while the corresponding range for Ni/Al$_2$O$_3$ was 360°–700° C. Thus the Ni/Al$_2$S$_3$ catalyst does indeed reduce at a lower temperature than does its alumina-based counterpart. Based on these data one might predict that reduction of the Ni/Al$_2$O$_3$ catalyst at a higher temperature would increase its activity. The data in Table IV indicate that this is not necessarily true. These data were obtained with a Ni/Al$_2$O$_3$ catalyst which was reduced at 900° F. The results are essentially the same as those obtained with the catalyst which was reduced at 700° F.

TABLE IV

SELECTIVE HYDROGENATION OF ISOPRENE WITH A Ni/Al$_2$O$_3$ CATALYST REDUCED at 900° F

| Hours On Stream | Temp. | ⟋⟍ | ⟋⟍ | ∥⟍ | ∥⟍ | ⟝⟍ | % Conv. | % Select. |
|---|---|---|---|---|---|---|---|---|
| 2.0 | 200 | .34 | .33 | .42 | 50.40 | .97 | 4.0 | 84 |
| 4.75 | 250 | .11 | .005 | .37 | 51.23 | 1.61 | 4.0 | 99.7 |
| 6.5 | 350 | .22 | .04 | 6.41 | 5.74 | 28.79 | 86.0 | 99.0 |
| 7.0 | " | .20 | .03 | 6.70 | 3.97 | 29.71 | 90.3 | 99.9 |
| 8.5 | " | 4.92 | .13 | 6.73 | 6.64 | 26.42 | 85.2 | 99.7 |
| 10.0 | 375 | 3.64 | .51 | 9.11 | 0.99 | 39.27 | 98.2 | 99.0 |

Pressure = 1000 psig
H$_2$/oil = 5.4
LHSV = 2.82
% Nickel = 9.81%

What is claimed is:

1. A process of selectively hydrogenating dienes present in a mixed hydrocarbon stream composed essentially of hydrocarbons in the range of 3–6 carbon atoms, said process comprising contacting said mixed hydrocarbon stream with added hydrogen at a temperature of between about 150° F and about 500° F and a pressure of about 1 to about 1000 atmospheres in the presence of a catalyst comprising about 1 to about 30% by weight nickel on an aluminum sulfide support.

2. A process according to claim 1 wherein said catalyst is prepared by:
 a. contacting an aluminum sulfide support with a nickel complex capable of decomposition to nickel metal under anhydrous conditions in the presence of an aprotic solvent;
 b. heating the solution from step (a) under refluxing conditions for between about 1 hour and about 10 hours;
 c. recovering the resulting nickel/aluminum sulfide catalyst from the solution; and
 d. calcining the nickel/aluminum sulfide catalyst at a temperature of between about 500° F and about 1000° F in an inert atmosphere.

3. A process according to claim 2 wherein said aluminum sulfide support is prepared by heating a solution of a trialkyl aluminum having 1 to 5 carbon atoms in an aprotic solvent with a stoichiometric amount of hydrogen sulfide under anhydrous conditions at a temperature of between about 100° F and about 400° F and a pressure of between about 100 psig and about 1000 psig.

4. A process according to claim 1 wherein said diene is isoprene.

5. A process according to claim 2 wherein said nickel complex is selected from the group consisting of nickel acetylacetonate, nickel octoate, bis-salicylaldoxime nickel, bis-salicylaldehyde nickel, bis-cyclooctadiene nickel and nickel chloride-tetrahydrofuran complex, bis($\pi$-allyl)nickel chloride, and bis(tetrahydrofuran)-nickel dibromide.

6. A process according to claim 5 wherein said nickel complex is nickel acetylacetonate.

7. A process according to claim 2 wherein said aprotic solvent is toluene.

8. A process according to claim 3 wherein said trialkyl aluminum is triethyl aluminum and said aprotic solvent is toluene.

* * * * *